United States Patent [19]

Adam, nee Chosson et al.

[11] 4,101,649

[45] Jul. 18, 1978

[54] HYDROSOLUBLE AGENTS HAVING NON SPECIFIC IMMUNODEPRESSIVE PROPERTIES

[75] Inventors: Arlette Adam, nee Chosson, Palaiseau; Pierre LeFrancier, Bures-sur-Yvette; Edgar Lederer, Sceaux, all of France

[73] Assignee: Agence Nationale de Valorisation de la Recherche (ANVAR), Neuilly-sur-Seine, France

[21] Appl. No.: 730,839

[22] Filed: Oct. 8, 1976

[30] Foreign Application Priority Data

Oct. 9, 1975 [FR] France ................ 75 30948

[51] Int. Cl.$^2$ ............... A61K 39/00; A61K 37/00; C07C 103/52
[52] U.S. Cl. .................... 424/12; 424/177; 260/112.5 R
[58] Field of Search ........... 260/112.5 R; 424/177, 424/12

[56] References Cited

U.S. PATENT DOCUMENTS 3,879,376   4/1975   Vanlerberghe et al. ...... 260/112.5 R

FOREIGN PATENT DOCUMENTS 2,450,355   10/1974   Fed. Rep. of Germany .... 260/112.5 R

OTHER PUBLICATIONS

Exhibit A, "Bacterial Membranes & Walls", 1973, pp. 39-41.
Exhibit B, J. Med. Chem. 9, 1966, pp. 971-973.
Exhibit C, "Symposium International", 1974, p. 7.
Exhibit D, J. Am. Chem. Soc., 1964, 86, 1880–1881.
Chem. Abst. Subject Index, 8th collective, 13860s.

*Primary Examiner*—Delbert R. Phillips
*Attorney, Agent, or Firm*—Weiser, Stapler & Spivak

[57] ABSTRACT

The invention relates to N-acetylmuramyl-D-alanyl-D-isoglutamine and to N-acetylmuramyl-L-alanyl-L-isoglutamine which possess immunosuppressive or immunodepressive properties, as well as to the pharmaceutical compositions containing one of said compounds in association with a pharmaceutical vehicle.

26 Claims, No Drawings

HYDROSOLUBLE AGENTS HAVING NON SPECIFIC IMMUNODEPRESSIVE PROPERTIES

The invention relates to hydrosoluble agents which are effective as non specific depressors of immunity for inhibiting within a host the immune responses to antigens of different kinds.

It is known that in a number of therapeutical treatments it is desirable to depress the immune responses of the host. Such is for instance the case for patients which were grafted with organs originating from different individuals. The immunodepressive products which are in use are generally toxic and interfere with the metabolism of all the cells, thereby having a systemic action.

The object of the invention is thus to provide new products having immunodepressive properties while being substantially devoid of the toxicities which characterize most of the immunodepressive agents known up to now.

The invention relates particularly to the new product which is formed of N-acetylmuramyl-D-alanyl-D-isoglutamine, which can also be designated by resorting to conventional chemical nomenclature:

2-(2-acetamido-2-deoxy-3-O-D-glucopyranose)-D-propionyl-D-alanyl-D-isoglutamine.

This new product possesses valuable immunodepressive properties having a non specific character.

Such immunosuppressive properties have also been found in one diastereo-isomer of the product according to the invention, said diastereo-isomer being formed by N-acetylmuramyl-L-alanyl-L-isoglutamine.

Accordingly the invention relates also to an immunosuppressive or immunodepressive drug, the active principle of which is formed either of the N-acetylmuramyl-D-alanyl-D-isoglutamine, or of the N-acetylmuramyl-L-alanyl-L-isoglutamine.

The preferred active principle of the drug according to the invention is the N-acetylmuramyl-D-alanyl-D-isoglutamine, the immunodepressive activity of which is greater than that of the N-acetylmuramyl-L-alanyl-L-isoglutamine.

The above defined compounds can also be designated by the following abbreviations:

Mur-N-Ac-D-Ala-D-Glu-α-NH₂
Mur-N-Ac-L-Ala-L-Glu-α-NH₂

Their formulae are respectively:

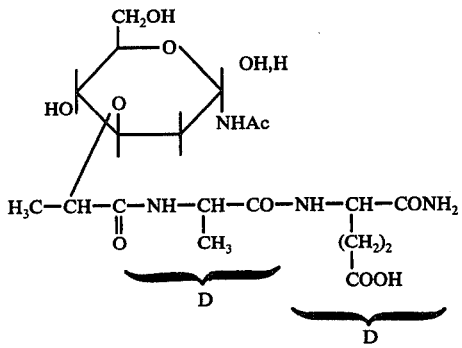

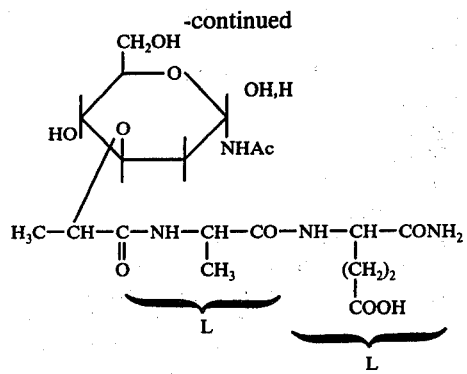

These products are substantially devoid of toxicity and form competing analogues of the adjuvants derived from the bacterial peptidoglycanes, more particularly of the N-acetylmuramyl-L-alanyl-D-isoglutamine, the adjuvant action of which, when administered within a water-oil emulsion, has already been disclosed in the French patent application Nr. 74 22909 of July 1st 1974, filed in the form of an application for a third certificate of addition to the main patent Nr. 71 41610 of Nov. 19, 1971, and later transformed into an application for an independent patent on Sept. 18 1975.

As has been brought to evidence by pharmacological tests which will be described hereafter, the said active principles of the drug according to the invention, and more specifically the new product according to the invention, i.e. N-acetylmuramyl-D-alanyl-D-isoglutamine, possess an action which is in antagonism with that of the N-acetyl-muramyl peptides which have an adjuvant action, such as N-acetylmuramyl-L-alanyl-D-isoglutamine. The first French application is an application on which is based pending U.S. patent application, Ser. No. 516,991 for Adam et al; the second application is an application on which there is based U.S. patent application Ser. No. 307,614, now U.S. Pat. No. 4,036,953 to Adam et al, issued on July 19, 1977.

The invention also relates more particularly to compositions containing the above said immunodepressive agents in the midst of a water-oil emulsion.

The above said immunodepressive agents can be produced by a process which comprises reacting N-acetylmuramic acid, the free —OH functions of which have been previously protected, except that of the propionyl group of the said acetyl-muramic acid, with the corresponding peptide the free —OH functions of which were equally previously protected, and then freeing the initially protected functions, such as by hydrolysis in an acid medium.

The invention also relates more particularly to the N-acetylmuramyl-D-alanyl-D-isoglutamine the otherwise free —OH functions of which are protected, either by benzyl groups or benzylidene groups.

An example of the production of the N-acetylmuramyl-D-alanyl-D-isoglutamine is described hereafter.

The Mur-N-Ac-D-Ala-D-Glu-α-NH₂, the chemical structure of which is: 2-(2-acetamido-2-deoxy-3-O-D-glucopyranose)-D-propionyl-D-alanyl-D-isoglutamine, is prepared in several steps. In a first stage, the peptidic chain is synthesized, and then, in a second stage, fixed on the muramyl derivative the free —OH functions of which have previously been protected, such as by benzyl or benzylidene groups. Thereupon, the protected functions are finally freed.

Hydrochloride of the benzylic ester of L-alanyl-D-isoglutamine acid (I).

The abbreviation BOC used hereafter designates the group t-butyloxycarbonyl group.

680 mg (3.4 m moles) of t-butyloxycarbonyl-D-alanyl acid (BOC-D-Ala-OH) were added under stirring to a solution of 1.09 g (4 m moles) of the hydrochloride of the benzylic ester of the D-isoglutamine and 0.45 ml (4 m moles) of N-dimethylmorpholine in dimethylformamide. 700 mg (3.4 m moles) of dicyclohexylcarbodiimide were added thereto. The reaction mixture was then left at ambient temperature for twelve hours. It was then concentrated to dryness. The dry residue was taken up into 50 ml of ethyl acetate and washed successively with a 10% solution of citric acid, with water and with a normal solution of sodium bicarbonate, finally with water. The ethyl acetate phase is dried on $MgSO_4$ and concentrated. Upon crystallizing in an ethyl acetate-petroleum ether mixture, 780 mg of the product were obtained (51% yield); MP 128°–130° C $[\alpha]_D^{25}$ = +25.3° in methanol. The product was then dissolved in 5 ml of a normal solution of hydrochloric acid in acetic acid. 30 minutes later the solution was concentrated to dryness and the residue taken up in the minimum amount of methanol. The product was precipitated with ether. 370mg (yield 56%). Mp 128°–130° $[\alpha]_D^{25}$ = +26° (methanol)

$C_{15}H_{22}O_4N_3Cl$ (343.82) Calculated % C = 52.4 — H: 6.45 — N: 12.2 found 52.53 6.60 12.25

2-(benzyl-2-acetamido-4,6-O-benzylidene-2-deoxy-3-O-β-D-glucopyranosyl)-D-propionyl-D-Ala (γ-O-benzyl)-D-Glu-α-NH$_2$ (II)

A solution of 157 mg of benzyl-2-acetamido-4,6-O-benzylidene-3-O-(D-1-carboxyethyl)-2-deoxy(β-D-glucopyranoside (I), (0.33 m moles) in an acetonitrile-N-N-dimethylformamide mixture (2 : 1, v/v, 5 ml) containing an equivalent amount (0.33 m moles) of triethylamine was poured into a suspension maintained at a temperature of 0° C of N-ethyl-5-phenylisoxazolium-3'-sulfonate (84.3 mg) (Woodward K reactant) in acetonitrile (5ml). The mixture was stirred at 0° C until a clear solution was obtained (after 1 hour 30 minutes approximately). A solution of the hydrochloride of the D-Ala-(γ-O-benzyl)D-Glu-α-NH$_2$ (II) (114,4 mg, 0.33 m moles) in an acetonitrile-N-N dimethylformamide mixture (2 : 1 v/v, 5 ml) containing an equivalent (0.33 m moles) of triethylamine was then added. After a night of stirring at ambient temperature the solvents were evaporated under vacuum, and the solid residue obtained carefully extracted with water in order to remove the side products. The solid was dried and crystallized in ethanol giving the (II) product: 550 mg. (yield 73%) — Mp 255°–257° —$[\alpha]_D^{25}$ = −30°, dimethylformamide 2-(2-acetamido-2-deoxy-3-O-D-glucopyranosyl)-D-Ala-D-Glu-α-NH$_2$ (III)

The compound (II) (200 mg) was suspended within a 60% acetic acid solution (15 ml) and heated for 1 hour at 100° C. After cooling of the solution, the acetic acid was evaporated under vacuum, the last residues of acid were removed by resorting to additions of water followed by evaporation and the water residues were finally removed by distillations in the presence of toluol. The residue obtained was subjected to chromatography on a column of silica gel (15 g) (chloroform-methanol, 6 : 1 v/v). The pure fractions were pooled, evaporated under vacuum, thereby leaving a residue having chromatographical purity, (120 mg, 73% ).

This compound (69 mg) was subjected to catalytical hydrogenation within glacial acetic acid (10 ml) in the presence of palladium on coal (25 mg). 3 hours later, the catalyst was dried and the filtrate evaporated under vacuum. The compound V was obtained which exhibited the following analytical data:

yield 73.4% —$\alpha_D^{25}$ = +58°, acetic acid $C_{19}H_{32}O_{11}N_4$—$0.5C_2H_5OH$(515.534) calculated % C 46.59 — H 6.84 — N 10.86 found 46.52 6.82 10.86

The diastero-isomer, that is Mur-N-Ac-L-Ala-L-Glu-α-NH$_2$ may of course be obtained in the same manner starting however initially from the BOC-L-alanyl-L-isoglutaminyl benzilic ester.

The compound 2-(2-acetamido-2-deoxy-3-D-glucopyranosyl)-D-propionyl-L-Ala-L-Glu-α-NH$_2$ was obtained with a yield of 22.5% from the coupling operation.

The analytical data of this compound were as follows:

M.P. 155°–160° C $[\alpha]_D^{25}$ = +29° (glacial acetic acid) $C_{19}H_{32}O_{11}N_4$·2.75 $H_2O$ (542) calculated % C 42.1 — H 6.8 — N 10.35 found 42.0 6.4 10.37

Pharmacological properties of the compound under consideration (1.) Determination of the innocuousness of the active principles of the drug according to the invention It was determined by the method disclosed by L. Chedid et al, Ann. N.Y. Acad.Sci.133:712, 1966. The products to be tested were administered intravenously to mice which had been previously surrenalectomized. Accordingly they had been rendered very sensitive.

It was however found that all mice survived after having been injected with doses of the product under study which are effective to produce the immunodepressing action found in the tests disclosed hereafter. Therefore the products or compounds according to the invention do exhibit excellent innocuousness.

(2. ) Immunodepressive properties of the agents according to the invention

In the two series of tests the results of which are indicated hereafter, the influence of the active principles of the drugs according to the invention on the antiovalbumin antibodies rate was studied under the following conditions.

Female Hartley guinea pigs of 300–350 g. were given in the plantar pad of each of the two rear paws an emulsion composed of equal parts of incomplete Freund's adjuvant and a physiological solution containing ovalbumin (5 mg/guinea pig) and the preparations to be tested. The Freund's incomplete adjuvant (FIA), the Freund's complete adjuvant (FCA) marketed by the DIFCO Company and N-acetylmuramyl-L-alanyl-D-isoglutamine were used as controls.

The rate of antibodies with respect to ovalbumin was determined three weeks later after the injection in the conditions which were indicated in the French patent Nr 71 41610 of Nov. 19, 1971; it is expressed in μg of the antigen-antibody precipitate per ml of serum at the point of equivalence.

In a second series of tests, the delayed hypersensivity to ovalbumin which produces a cutaneous reaction was measured four weeks after the injection; it is expressed by the diameter in millimetres of the erythema (E), of the induration (I) or of the necrosis (N), 48 hours after the sub-cutaneous injection of 50 micrograms of ovalbumin.

The results of the first series of tests is indicated in table I hereafter. They bring to evidence the immunodepressive properties of the two compounds tested, the activity measured being above all remarkable as concerns N-acetylmuramyl-D-alanyl-D-isoglutamine.

As this can be read from Table I, compounds according to the invention do possess an action which is opposite of that of N-acetylmuramyl-L-alanyl-D-isoglutamine, which, in the contrary, is shown to possess a marked adjuvant activity.

The results of the second series of tests are indicated in Table II. Seven tests were made with the agent or agents to be tested, the latter being identified in the left column of the table.

The most significant results of table II are those

The study of table II as concerns the action of the immunodepressive agent taken alone compared to those of the Freund's incomplete adjuvant (FIA) could lead one to consider that the product according to the invention does not, prima faciae, possess any adjuvant property. This cannot apply to table I from which it appears that Mur-N-Ac-L-Ala-L-Glu-α-$NH_2$ and even more importantly Mur-N-Ac-D-Ala-D-Glu-α-$NH_2$ do induce antiovalbumin antibodies rates much lower than those which were measured in animals which had received the Freund's incomplete adjuvant only. The hypothesis can be formulated that in the first series of tests the animals tested were suffering a slight infection, which consequently might have been at the outset of the discovery of the immunodepressive properties of the active principles according to the invention. As this has

TABLE I

| Compounds | Doses (μg/aninmal) | Rate of antiovalbumin antibodies (μg proteins / ml serum) | | | | | | | mean values |
|---|---|---|---|---|---|---|---|---|---|
| 1 Freund's incomplete Adjuvant (FIA) | — | 4200 | 3800 | 1720 | 5200 | 3100 | 2940 | 4200 | 3592 |
| 2 Freund's complete Adjuvant (FCA) | 50 | 11200 | 8400 | 6960 | 11040 | 10400 | 9200 | 4800 | 8856 |
| 3 Mur-N-Ac-L-Ala-D-Glu$_r$α-$NH_2$ + FIA | 25 | 9280 | 11200 | 12000 | 11600 | 12000 | 11600 | 9280 | 10992 |
| 4 Mur-N-Ac-L-Ala-D-Glu$_r$α-$NH_2$ + FIA | 10 | 15500 | 11000 | 9520 | 14000 | 4480 | 15000 | 10600 | 11440 |
| 5 Mur-N-Ac-D-Ala-D-Glu$_r$α-$NH_2$ + FIA | 25 | 200 | 800 | 900 | 1300 | 1900 | 900 | 1500 | 1068 |
| 6 Mur-N-Ac-L-Ala-L-Glu$_r$α-$NH_2$ + FIA | 25 | 2800 | 1140 | 3400 | 4200 | 1700 | 800 | 700 | 2104 | corresponding to tests 3, 5 and 6 which clearly bring to evidence the competitive and antagonistic actions of the excellent adjuvant agent consisting of the Mur-N-Ac-L-Ala-D-Glu-α-$NH_2$ (test Nr 3) and of the product according to the invention, more precisely Mur-N-Ac-D-Ala-D-Glu-α-$NH_2$ (tests Nr 5 and 6). When the product according to the invention and the adjuvant agent are administered simultaneously, it can be seen that the former strongly inhibits the adjuvant action of the latter.

been showed hereabove, this immunodepressive action has been confirmed in a strong manner by the bringing into play of the antagonistic actions of Mur-N-Ac-D-Ala-D-Glu-α-$NH_2$ and of Mur-N-Ac-L-Ala-D-Glu-α-$NH_2$.

Owing to their immunodepressive properties the compounds according to the invention do therefore form valuable active principles for the production of immunodepressive

| Compounds | Doses (μg/animal) | Rate of antiovalbumin antibodies (μg proteins/ ml serum) | mean values | Delayed hypersensibility 50 μg ovalbumine/animal |
|---|---|---|---|---|
| 1 FIA | 0 | 2200 | | 5 N / 5 I |
| | | 780 | | 0 |
| | | 2500 | 1553 | 0 |
| | | 1440 | | |
| | | 1600 | | 5 N / 5 I |
| | | 800 | | 0 |
| 2 FCA | 50 | 7200 | | 5 N / 15 I |
| | | 4800 | | 12 I |
| | | 3300 | 4950 | 5 N / 12 I |
| | | 4800 | | 5 N / 15 I |
| | | 4800 | | 5 N / 15 I |
| | | 4800 | | 10 N / 15 I |
| 3 Mur-N-Ac-Ala-D-Glu$_r$α-$NH_2$ | 10 | 8000 | | 5 N / 15 I |
| | | 9500 | | 5 N / 15 I |
| | | 6500 | | 7 N / 16 I |
| | | 7500 | 7717 | 7 N / 17 I |
| | | 6800 | | 6 N / 20 I |
| | | 8000 | | 8 N / 20 I |
| 4 Mur-N-Ac-D-Ala-D-Glu$_r$α-$NH_2$ | 25 | 1720 | | 0 |
| | | 660 | | 0 |
| | | 3600 | | 5 N / 12 I |
| | | 1800 | 1890 | 5 N |
| | | 1800 | | 0 |
| | | 1760 | | 0 |
| 5 Mur-N-Ac-L-Ala-D-Glu-,α-$NH_2$ | 10 | 1600 | | 12 I |
| + | + | 4200 | | 5 N / 10 I |
| Mur-N-Ac-D-Ala-D-Glu-α-$NH_2$ | 25 | 5600 | 3400 | 4 N / 18 I |
| | | 2400 | | 4 N / 12 I |
| | | 4500 | | 5 N / 12 I |
| | | 2100 | | 5 N / 12 I |
| 6 Mur-N-Ac-L-Ala-D-Glu$_r$α-$NH_2$ | 10 | 1900 | | 4 N / 12 I |
| + | + | 3700 | | |
| Mur-N-Ac-D-Ala-D-Glu$_r$α-$NH_2$ | 10 | 6400 | 4917 | 4 N / 12 I |
| | | 6000 | | 5 N / 15 I |
| | | 5900 | | 12 I |
| | | 5600 | | 3 N / 12 I |
| 7 Mur-N-Ac-D-Ala-D-Glu$_r$α-$NH_2$ | 100 | 950 | | |
| | | 1000 | 1050 | 5 E |
| | | 1200 | | 0 | drugs useful for the treatment of pathological conditions which bring into play excessive immune responses with respect to particular antigens or foreign bodies willingly introduced into the organism of the host. Particularly the invention relates to pharmaceutical compositions useful for the treatment of a host which has been grafted with organs originating from a different host, for the sake of reducing the immune responses of the organism with respect to the grafted organ.

The invention also relates to injectable compositions containing efficient doses of the compounds under consideration, notably in a water-in-oil stabilized emulsion, the oil being preferably of a vegetal origin, particularly when its administration in man is considered.

For instance the vegetable emulsion used is formed starting from about 2 to about 6 volumes of an isotonic aqueous solution, particularly a sterile injectable solution, 10 parts of a vegetal metabolizable oil and, in addition thereto, non-immunogenic proteins, for instance of the serum-albumin- or globulin-type, in proportion sufficient to impart stability to the emulsion formed. For instance this emulsion contains from about 30 to about 150 mg, preferably from about 40 to about 120 mg, and even more particularly 60 mg of proteins per ml of the aqueous phase.

The proteins which dissolve in the aqueous phase can of course themselves contribute to the isotonocity of the latter. If need be the aqueous phase may comprise in addition appropriate proportions of other agents likely to contribute to said isotonicity, for instance sodium chloride, glucose, dextrans, etc.

The compounds which have been described do also form valuable laboratory reactants because of their antagonistic action with respect to agents effective as immunological adjuvants, for stimulating in a host immune responses to antigens of different kinds, such as for instance N-acetylmuramyl-L-alanyl-D-isoglutamine. Accordingly, they can be used as agents enabling the nature of the adjuvant action of substances under study to be verified or confirmed.

We claim:

1. N-acetylmuramyl-D-alanyl-D-isoglutamine which possesses immunosuppressive or immunodepressive properties.

2. N-acetylmuramyl-D-alanyl-D-isoglutamine, the free -OH functions of which are protected either by benzyl groups, or by benzylidene groups.

3. A pharmaceutical composition useful for causing an immunosuppressive response in a host subject to an excessive immune response to an antigen, which comprises an active immunosuppressive compound selected from the group consisting of N-acetylmuramyl-D-alanyl-D-isoglutamine or of N-acetylmuramyl-L-alanyl-L-isoglutamine, in association with a pharmaceutical carrier, the compound being present in an immunosuppressive amount.

4. A pharmaceutical composition useful for causing an immunosuppressive response in a host subject to an excessive immune response to an antigen, wherein the active immunosuppressive compound selected from the group consists of N-acetylmuramyl-D-alanyl-D-isoglutamine in association with a pharmaceutical carrier, the compound being present in an immunosuppressive amount.

5. An injectable pharmaceutical composition useful for causing an immunosuppressive response in a host subject to an excessive immune response to an antigen, wherein the active immunosuppressive compound selected from the group consists of N-acetylmuramyl-D-alanyl-D-isoglutamine or of N-acetylmuramyl-L-alanyl-L-isoglutamine, said active compound being associated with an injectable liquid vehicle, the compound being present in an immunosuppressive amount.

6. A composition according to claim 5 wherein the injectable liquid vehicle is a stabilized emulsion of the water-in-oil type.

7. A composition according to claim 6 wherein the oil is a vegetable oil.

8. The pharmaceutical composition useful for causing an immunosuppressive response in a host subject to an excessive immune response which comprises a water-in-oil stabilized emulsion and a compound selected from the group consisting of N-acetylmuramyl-D-alanyl-D-isoglutamine and N-acetylmuramyl-L-alanyl-L-isoglutamine in an amount effective to cause an immunosuppressive response to an antigen in the host.

9. The pharmaceutical composition of claim 8 wherein the compound is N-acetylmuramyl-D-alanyl-D-isoglutamine.

10. The pharmaceutical composition of claim 8 wherein the compound is N-acetylmuramyl-L-alanyl-L-isoglutamine.

11. The pharmaceutical composition of claim 8 wherein the vegetable oil is vegetable and metabolisable.

12. The pharmaceutical composition of claim 8 wherein the emulsion comprises a non-immunogenic protein.

13. The pharmaceutical composition of claim 12 which is isotonic, sterile and injectable.

14. An injectable solution useful for causing an immunosuppressive response in a host subject to an excessive immune response to an antigen comprising an immunodepressive effective amount of a compound selected from the group consisting of N-acetylmuramyl-D-alanyl-D-isoglutamine and N-acetylmuramyl-L-alanyl-L-isoglutamine in a water-in-oil stabilized emulsion.

15. A diagnostic composition for diagnosis and inhibition of the action of an adjuvant comprising a compound selected from the group consisting of: N-acetylmuramyl-D-alanyl-D-isoglutamine and N-acetylmuramyl-L-alanyl-L-isoglutamine and a compatible carrier.

16. A therapeutical method for controlling immunological responses to an antigen within a host which comprises adminstering to the host therapeutical composition comprising a compound selected from the group consisting of: N-acetylmuramyl-D-alanyl-D-isoglutamine and N-acetylmuramyl-L-alanyl-L-isoglutamine and a pharmaceutically acceptable carrier, the compound being in an amount effective to cause an immunodepressive response to an antigen in the host.

17. The method of claim 16 wherein the carrier is a water-in-oil stabilized emulsion.

18. The method of claim 16 wherein the adminstration is for the treatment of a pathological condition caused by an excessive immune response in a patient grafted with an organ from a different individual.

19. The solution of claim 14 wherein the compound is N-acetylmuramyl-D-alanyl-D-isoglutamine.

20. The solution of claim 14 wherein the compound is N-acetylmuramyl-L-alanyl-L-isoglutamine.

21. The method of claim 16 wherein the compound is N-acetylmuramyl-D-alanyl-D-isoglutamine.

22. The method of claim 16 wherein the compound is N-acetylmuramyl-L-alanyl-L-isoglutamine.

23. The method of claim 18 wherein the compound is N-acetylmuramyl-D-alanyl-D-isoglutamine.

24. The method of claim 18 wherein the compound is N-acetylmuramyl-L-alanyl-L-isoglutamine.

25. The composition of claim 8 wherein the compound is N-acetylmuramyl-D-alanyl-D-isoglutamine.

26. The composition of claim 8 wherein the compound is N-acetylmuramyl-D-alanyl-D-isoglutamine.

* * * * *

UNITED STATES PATENT AND TRADEMARK OFFICE
CERTIFICATE OF CORRECTION

PATENT NO. : 4,101,649
DATED : July 18, 1978
INVENTOR(S) : Arlette Adam, nee Chosson, Pierre LeFrancier, Edgar Lederer It is certified that error appears in the above—identified patent and that said Letters Patent is hereby corrected as shown below:

Column 10, claim 26 should read:

26. The composition of claim 8 wherein the compound is N-acetylmuramyl-L-alanyl-L- isoglutamine.

Signed and Sealed this

First Day of December 1981

[SEAL]

Attest:

Attesting Officer

GERALD J. MOSSINGHOFF

Commissioner of Patents and Trademarks